United States Patent
Keppel et al.

(10) Patent No.: US 8,669,541 B2
(45) Date of Patent: Mar. 11, 2014

(54) HADRON TREATMENT PLANNING WITH ADEQUATE BIOLOGICAL WEIGHTING

(71) Applicant: Hampton University, Hampton, VA (US)

(72) Inventors: Cythnia E. Keppel, Norfolk, VA (US); Richard A. Britten, Virginia Beach, VA (US); Vahagn R. Nazaryan, Newport News, VA (US)

(73) Assignee: Hampton University, Hampton, VA (US)

( * ) Notice: Subject to any disclaimer, the term of this patent is extended or adjusted under 35 U.S.C. 154(b) by 0 days.

(21) Appl. No.: 14/019,737

(22) Filed: Sep. 6, 2013

(65) Prior Publication Data

US 2014/0012062 A1 Jan. 9, 2014

Related U.S. Application Data

(63) Continuation of application No. 13/168,441, filed on Jun. 24, 2011, now Pat. No. 8,546,774, which is a continuation of application No. 12/466,979, filed on May 15, 2009, now Pat. No. 7,982,200, which is a continuation of application No. 11/727,584, filed on Mar. 27, 2007, now Pat. No. 7,550,752.

(60) Provisional application No. 60/786,402, filed on Mar. 28, 2006.

(51) Int. Cl.
*A61N 5/06* (2006.01)

(52) U.S. Cl.
CPC ......................................... *A61N 5/06* (2013.01)
USPC .................................... 250/492.3; 250/505.1

(58) Field of Classification Search
USPC .......................................... 250/492.3, 505.1
See application file for complete search history.

(56) References Cited

U.S. PATENT DOCUMENTS 7,268,358 B2 * 9/2007 Ma et al. .................... 250/492.3
8,080,801 B2 * 12/2011 Safai ............................ 250/368
8,183,541 B2 * 5/2012 Wilkens et al. ............ 250/492.1

FOREIGN PATENT DOCUMENTS

| JP | 10-314323 | 2/1998 |
| WO | 2004/109717 | 12/2004 |
| WO | 2005/057738 | 6/2005 |
| WO | 2007/090798 | 8/2007 |

OTHER PUBLICATIONS

Japanese Notice of Reasons for Refusal Report issued in corresponding Japanese Patent Application No. 2009-502931 issued Jul. 31, 2012 and an English translation of thereof.

* cited by examiner

*Primary Examiner* — Kiet T Nguyen
(74) *Attorney, Agent, or Firm* — McGuireWoods, LLP (57) ABSTRACT

Treatment planning methods are provided that determine the variability of relative biological effectiveness (RBE) along a beam line and calculate, among other things, what intensity of hadron beam such as a proton or a carbon ion beam should be applied to achieve a desired biological dose at treatment site of a patient afflicted with a medical condition. Typically, three or four RBE values at three or four corresponding spacially-dispersed intervals along the beam line are calculated. In one embodiment, two RBE values for the spread-out Bragg peak (SOBP) region of the treatment site; one for the proximal section and one for the declining distal section is calculated. A third and different RBE value may be determined for the distal edge region of the SOBP. A fourth value may also be calculated for a pre-SOBP region.

10 Claims, 5 Drawing Sheets

HADRON TREATMENT PLANNING WITH ADEQUATE BIOLOGICAL WEIGHTING

CROSS-REFERENCE TO RELATED APPLICATIONS

This is a continuation application of co-pending U.S. patent application Ser. No. 13/168,441, filed Jun. 24, 2011, which is a continuation application of U.S. patent application Ser. No. 12/466,979, filed May 15, 2009, now issued as U.S. Pat. No. 7,982,200 on Jul. 19, 2011, which is a continuation of U.S. patent application Ser. No. 11/727,584, filed Mar. 27, 2007, now issued as U.S. Pat. No. 7,550,752 on Jun. 23, 2009, which claims the benefit under 35 U.S.C. 119(e) of U.S. Provisional Application No. 60/786,402, filed Mar. 28, 2006, the disclosure of which is incorporated by reference herein in its entirety.

BACKGROUND OF THE INVENTION

1. Field of the Invention

The invention is generally related to methods of treatment planning using radiotherapy, and more particularly to methods of treatment planning with adequate biological weighting using hadron and/or proton beam radiotherapy.

2. Related Art

In recent years there has been a steady increase in clinical use of high energy hadron beams for patients afflicted with tumors and other medical conditions. It has been long known that protons differ from conventional radiation (photons, electrons) in their biological effectiveness. That is, to cause the same biological effect a lower dose of protons is required. Therefore, protons are more biologically effective. The relative biological effectiveness (RBE) is defined as the ratio of dose of reference radiation to the proton dose required to achieve the same biological effect.

In current clinical practice with therapeutic proton beams, a single RBE value (typically 1.1) is applied to all treatment plans, irrespective of depth of penetration, tissue, or any other particulars of the treatment. This is because previous studies indicated that RBE values were small in magnitude and because the variability of RBE with treatment parameters was believed to be within 10-20%. It was concluded that this variability was small relative to uncertainties associated with RBE values. New studies, however, reveal that the RBE variations can be as large as 100-300%, especially in the penumbra of the treatment volume delineation ("TVD"), e.g., the outline of the volume that conforms to the shape of the tumor.

Proton radiotherapy may use either mono-energetic proton beams or poly-energetic proton beams. Mono-energetic proton beams are characterized by a peak in their depth-dose distribution. This so-called Bragg peak is a result of an increasing energy deposition with the depth of penetration, leading to a maximum at the end of range of the proton beam. To obtain a good physical dose distribution for radiotherapy applications, the Bragg peak is spread out by passive or active beam modulation techniques to cover the target volume of a treatment site. Modulated beam profiles have a central flat region, which is used for treatment. A passive beam modulation technique utilizes scattering material placed upstream to change the beam energy. An active beam modulation technique changes the beam energy electronically.

Poly-energetic proton beams are characterized by variations in the amounts of energy delivered and by a three-dimensional localization of the dose. Moreover, non-uniform dose distributions from each poly-energetic proton beam may superimpose to give a desired dose in a target volume.

Beam modulation generates a broad spectrum of energies within the target volume, with the mean energy of protons decreasing with penetration distance. This results in a corresponding variation in linear energy transfer (LET), which increases with the depth of penetration. A biological dose deposited by the protons can be described as a product of proton fluence and LET. Thus, in proton beam radiotherapy a highly conformal high dose region is achieved by varying the proton fluence, and the energy spectrum, which is the essence of beam modulation. This highly conformal high dose region is the so-called spread-out Bragg peak (SOBP).

Determination of proton RBE at different points along the SOBP has been done in many centers, such as Cyclotron Research Center at Louvain-La Neuve and TRIUMF Cyclotron Research Center. Data has been reported on modulated proton beams with energies less than 100 MeV. These experiments used different approaches to assess the proton RBE, but all of them show that the RBE increases with depth within SOBP, with values ranging from 1.1 to 2.5.

Proton RBE depends on a number of factors including the type of tissue and the biological end point, the initial proton energy, the energy spread of the input proton beam, the depth of beam penetration, and the beam modulation technique. The RBE has been shown to increase with depth within the SOBP both theoretically and experimentally. This is partially attributed to the fact that the average proton energy decreases with depth within the SOBP. There are fewer investigations of the region beyond the distal point of the SOBP. These studies conclude that the RBE values continue to increase at the declining distal edge of the SOBP.

Recent studies irradiated human tumor SCC25 cells with a 65-MeV proton beam. Five positions along the beam line were simulated using Perspex plates of different thickness: one position, corresponding to the beam entrance, with 2 mm thick perspex, two along the SOBP at 15.6 and 25 mm, and two more measurements at the declining distal edge at 27.2 and 27.8 mm. Clonogenic survival of the irradiated cells and of their progeny was determined at various dose values at each position. Cobalt 60 (hereinafter, "$^{60}$Co") γ-rays were used as the reference radiation in this study.

RBE values obtained in this study increased with increasing depth. At the proximal part of SOBP, the RBE was evaluated to be close to 1.0. It reached the 1.2 value at the distal part of SOBP. Within the declining edge it continued to increase, and reached the value of about 1.4 at 27.2 mm, and 2 at 27.8 mm, where the relative dose was about 50% of that at the peak value. These RBE values were evaluated at the survival level given by 2 Gy γ-rays. For the progeny of irradiated cells, the RBE values were similar. The incidence of delayed effects increased with dose and with the depth within the beam. The results of this study show that at the distal declining edge of the beam, the RBE values increase significantly to an extent that is of practical significance when the region of treatment volume is close to sensitive tissues.

A second study was performed using the 62-MeV proton beam of the CATANA (Centro di Adro Terapia e Applicazzioni Nucleari Avanzati) facility. Cell survival of a resistant HTB140 human melanoma cell line was studied using various biological assays, at several depths along the SOBP, and at the declining distal edge. The three different assays used in this study were the clonogenic assay, the microtetrasolium assay, and the sulforhodamine B assay. To simulate different positions along the beam line, Perspex plates of various thicknesses were interposed. Cell samples were irradiated at 6.6, 16.3, 25, and 26 mm depths. The distal end of SOBP was at the depth of 25 mm that had a corresponding 102±3% relative dose, while the relative dose along the declining distal edge at 26 mm was 32±4%.

Surviving fractions at 2 Gy (SF2) were obtained throughout the whole SOBP, which indicated high level of radioresistance of these cells. The RBE at 2 Gy was used to analyze the efficiency of proton irradiation to inactivate cells as compared to conventional γ-ray radiation.

The results of this study again showed considerable increase in RBE values when approaching the distal end of SOBP. It was found that at the declining distal edge of SOBP, where the relative dose was ≈32%, the killing ability of protons was close to that observed at the distal end of SOBP, where the relative dose was ≈102%. The RBE at this depth on declining distal edge was found to be close to 4, using the clonogenic assay, and close to 3, using the sulforhodamine B assay. For reference, the RBE at the proximal part of SOBP was found to be close to 1.3, using both clonogenic and sulforhodamine B assays.

Results of the two studies discussed above evidence the importance of additional investigations of RBE along the SOBP, and in particular, at its declining distal edge. These findings also establish the necessity of development of treatment planning methods, which will incorporate adequate proton RBE's.

SUMMARY OF THE INVENTION

The invention satisfies the foregoing needs and avoids the drawbacks and limitations of the prior art by providing a system and methods for a treatment planning that determines the variability of RBE along the beam line and calculates, among other things, what intensity of proton beam should be applied to achieve a desired biological dose at treatment site of a patient afflicted with a medical condition.

In one aspect, a method for ensuring optimal biological effectiveness of a treatment beam at a treatment site of a patient is provided that includes the steps of determining a variability of relative biological effectiveness (RBE) along a line of each of a plurality of hadron beams, calculating RBE values at a plurality of sections of a spread-out Bragg peak (SOBP) associated with the treatment site, wherein the calculating takes into account the determined variability, and adjusting an intensity and energy of each of the plurality of hadron beams at each of the plurality of sections of the spread-out Bragg peak (SOBP) based on respective calculated RBE values for each of the plurality of sections to provide a calculated dose distribution for each of the plurality of sections, wherein the plurality of sections include a proximal part of SOBP area of the treatment site, a distal part of the SOBP, and a declining distal edge part of the SOBP, and wherein the calculated dose distributions superimpose to provide a desired dose at the treatment site.

In another aspect, a method for ensuring adequate biological effectiveness at a treatment site of a patient is provided that includes the steps of determining a variability of relative biological effectiveness (RBE) along a line of each of a first proton beam, a second proton beam, a third proton beam, and a fourth proton beam, calculating a first RBE value at a pre-plateau part of a spread-out Bragg peak (SOBP) of the treatment site, a second RBE value at a proximal part of SOBP, a third RBE value at a distal part of the SOBP, and a fourth RBE value at a declining distal edge part of the SOBP. The method also includes the steps of adjusting an intensity and energy of the proton beam at the pre-plateau part of the SOBP based on the first RBE value to provide a first dose distribution, adjusting an intensity and energy of the proton beam at the proximal part of the SOBP based on the second RBE value to provide a second dose distribution, adjusting an intensity and energy of the proton beam at the distal part of the SOBP based on the third RBE value to provide a third dose distribution, and adjusting an intensity and energy of the proton beam at a declining distal edge part of the SOBP based on the fourth RBE value to provide a fourth dose distribution, wherein the first, second, third and fourth dose distributions superimpose to provide a desired dose at the treatment site.

In another aspect, a method for ensuring adequate biological effectiveness at a treatment site of a patient is provided that includes the steps of defining geometric parameters of the treatment site, optimizing a biological dose distribution taking into account different relative biological effectiveness (RBE) values at a plurality of sections associated with the treatment site characterized by a spread-out Bragg peak (SOBP) and as defined by the geometric parameters, and delivering an optimized biological dose by hadron radiotherapy to the plurality of sections, wherein the plurality of sections include a declining distal edge part of the SOBP and at least one of the following parts: a proximal part of the SOBP, a distal part of the SOBP.

In another aspect, a method for delivering a biological dose at a treatment site of a patient is provided that includes the steps of determining a variability of relative biological effectiveness (RBE) along a line of each of a plurality of hadron beams, calculating RBE values at a plurality of sections of a spread-out Bragg peak (SOBP) associated with the treatment site, wherein the calculating takes into account the determined variability, and adjusting an intensity and energy of each of the plurality of hadron beams at each of the plurality of sections of the spread-out Bragg peak (SOBP) based on respective calculated RBE values for each of the plurality of sections to provide a calculated dose distribution for each of the plurality of sections, wherein the plurality of sections include a declining distal edge part of the SOBP and at least one of: a proximal part of the SOBP, a distal part of the SOBP and a pre-plateau portion of the SOBP, and wherein the calculated dose distributions superimpose to provide a desired dose at the treatment site.

In yet another aspect, an apparatus for ensuring optimal biological effectiveness of a treatment beam at a treatment site of a patient is provided that includes a first component to determine a variability of relative biological effectiveness (RBE) along a line of each of a plurality of hadron beams, a second component to calculate RBE values at a plurality of sections of a spread-out Bragg peak (SOBP) associated with the treatment site, taking into account the determined variability, and a third component to adjust an intensity and energy of each of the hadron beams at each of the plurality of sections of the spread-out Bragg peak (SOBP) based on respective calculated RBE values for each of the plurality of sections to provide a calculated dose distribution for each of the plurality of sections, wherein the plurality of sections include a proximal part of SOBP area of the treatment site, a distal part of the SOBP, and a declining distal edge part of the SOBP, and wherein the calculated dose distributions superimpose to provide a desired dose at the treatment site.

Additional features, advantages, and embodiments of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention. No attempt is made to show structural details of the invention in more detail than may be necessary for a fundamental understanding of the invention and the various ways in which it may be practiced. In the drawings.

DETAILED DESCRIPTION OF THE INVENTION

The embodiments of the invention and the various features and advantageous details thereof are explained more fully with reference to the non-limiting embodiments and examples that are described and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein. Descriptions of well-known components and processing techniques may be omitted so as to not unnecessarily obscure the embodiments of the invention. The examples used herein are intended merely to facilitate an understanding of ways in which the invention may be practiced and to further enable those of skill in the art to practice the embodiments of the invention. Accordingly, the examples and embodiments herein should not be construed as limiting the scope of the invention, which is defined solely by the appended claims and applicable law. Moreover, it is noted that like reference numerals represent similar parts throughout the several views of the drawings.

It is understood that the invention is not limited to the particular methodology, protocols, devices, apparatus, materials, applications, etc., described herein, as these may vary. It is also to be understood that the terminology used herein is used for the purpose of describing particular embodiments only, and is not intended to limit the scope of the invention. It must be noted that as used herein and in the appended claims, the singular forms "a," "an," and "the" include plural reference unless the context clearly dictates otherwise.

Unless defined otherwise, all technical and scientific terms used herein have the same meanings as commonly understood by one of ordinary skill in the art to which this invention belongs. Preferred methods, devices, and materials are described, although any methods and materials similar or equivalent to those described herein can be used in the practice or testing of the invention. Although the description herein primarily uses protons and proton beams for exemplary descriptions, it should be understood that other types of hadron radiotherapy may be employed as well, such as carbon ion radiotherapy. Therefore, the examples and Figures include these other types of hadron radiotherapy.

Figure 1:
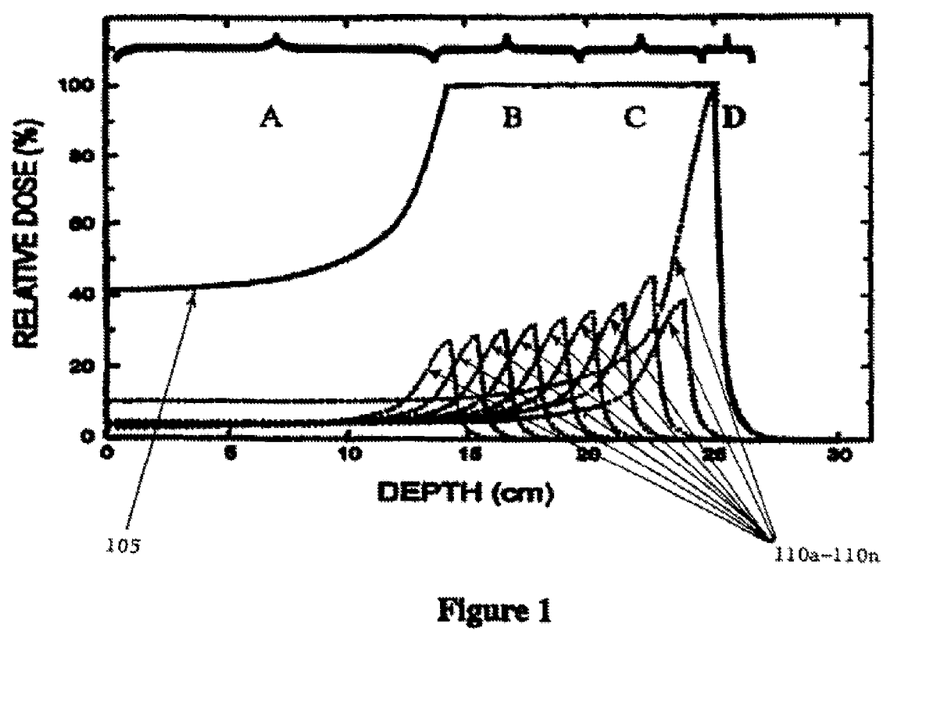
FIG. 1 is an exemplary graph showing depth dose distribution for a spread-out Bragg peak (SOBP), according to principles of the invention.

One aspect of the invention provides a treatment planning method that determines the variability of RBE along the proton beam line and calculates, among other things, what intensity of proton beam should be applied to achieve a desired dose at treatment site typically of a patient afflicted with a medical condition. FIG. 1 is an exemplary graph showing depth versus dose distribution for a spread-out Bragg peak (SOBP), according to principles of the invention. This SOBP is associated with a treatment site. In this embodiment, typically four RBE values at four corresponding spacially-dispersed intervals along the beam line are considered, shown in FIG. 1 as sections or parts under brackets labeled "A", "B", "C" and "D." In FIG. 1, the section under the bracket labeled "A" of the irradiated volume is referred to as the pre-SOBP section. The section under the bracket labeled "B" of the irradiated volume is referred to as the proximal SOBP section. The section under the bracket labeled "C" of the irradiated volume is referred to as the distal SOBP section, and the section under the bracket labeled "D" of the irradiated volume is referred to as the declining distal SOBP section. The curve labeled 105 represents a proton's depth dose profile after a plurality of individual proton beams have been modulated to yield the constant dose region referred to as the SOBP. The curves labeled as $110a$-$110n$ represent depth dose profiles of a subset of proton beams whose energies and intensities have been modulated to yield the constant dose region referred to as the SOPB region. In some embodiments, fewer than four sections may be considered.

Illustratively, the method may determine two RBE values for the SOBP region (sections B and C in FIG. 1) of the treatment site; one for the proximal section B, and one for the distal section C. A third and different RBE value may be determined for the declining distal edge region (section D in FIG. 1). Determining the third RBE value (section D) is often important to take into account that the level of cell killing several millimeters beyond the distal part (at low energies) is still comparable with that at the proximal part of the SOBP region. At higher energies (>200 MeV), determination of the RBE in section D may be even more essential, because the spatial extent of this section can typically be a couple of centimeters long.

Determination of the RBE in section A (i.e., the pre-plateau section) may also be of special significance, although not always necessary. This section falls in the normal tissue area, and it is known that the biological weighting leads to a predicted increase in normal tissue complication probability. Fortunately, however, there have not yet been any clinical studies reporting substantial normal tissue complications. As outlined above, however, the combination of higher RBE values and wider distal edges of high energy beams in conformal treatment plans may result in this becoming a significant issue.

Regarding the RBE values associated with higher (>200 MeV) energy proton beams, the LET of the attenuating high energy protons may be proportionally higher than that observed with the 60-66 MeV protons, and thus the RBE values in the very distal portion of the SOBP region may also be even higher.

Once the higher energy RBE values have been obtained, they may be substituted into a computer executable treatment algorithm to verify what physical and biological dose distributions are adequate for medical treatment using an animal model.

An algorithm that maps the 3-dimensional biological depth-dose profile of proton therapy beams with variable incident energies may be used to determine the RBE values at different locations along the proton's depth-dose profile. This algorithm typically uses a model for bio-response calculations for use in clinical applications. Both a simple phenomenological model based on α,β values (linear-quadratic model) and more sophisticated truck structure models (Amorphous Track Partition (ATP) and Amorphous Track Local effect (ATL), and possibly their combination) may be used for accurate quantitative evaluation of bio-response of tumors and normal tissues to proton radiation.

Biologic depth-dose profiles calculated with different models may be checked against each other, and with the cell-survival data and, more importantly, against in vivo measurement results to make sure there is satisfactory agreement, and for optimization.

RBE depends on the structure of the physical energy deposition, on biological response, and production of primary DNA lesions. RBE may also have significant dependence on the repair capacity of the affected cells and tissue although the RBE of fast neutrons proved to be independent of repair capacity. Additionally, RBE depends on the effect level and is larger for high survival levels and decreases with decreasing survival. The linear-quadratic model is one example of a survival parameterization, given by:

$$S = S_0 e^{-(\alpha D + \beta D^2)}, \quad (1)$$

with $S$, $S_0$ survival (0 indicating initial) and $D$ the dose. Since $RBE = dose_{x-ray}/dose_p$ for the same level of effect, the ratio of x-ray and proton α values gives the highest RBE value, $$RBE = \frac{\alpha_p}{\alpha_{x-ray}}. \quad (2)$$

RBE is also strongly correlated to the experimental α/β ratio. This correlation is particularly strong for carbon ions. Thus, models intended to calculate the RBE values typically have to include α/β ratios. These arguments can also help to identify tumors that are the most important candidates for hadron therapy. These are tumors of high radio-resistance that usually can be characterized by small α/β ratio and thus show the highest RBE values since RBE is typically measured relative to photons. The normal tissue sparing and therefore dose escalation potential of proton therapy is particularly promising for such tumors.

Integration of truck structure models into clinical treatment planning algorithms has practical limitations due to high demands for computing time and memory. Therefore, the truck structure model for protons should be simplified, which may be accomplished via the use of a similar approximation to that used in the "local effect model," developed and successfully applied at GSI for Carbon ions. Namely, the biological effect due to a single traversal (direct or indirect) of the cell nucleus by the charged particle depends weakly on the "impact parameter" (line of closest approach of the particle track to the center of the nucleus). Thus, a zero impact parameter can be used that greatly reduces the stochastic fluctuation in energy deposition. The integrity of this can be carefully checked by comparison of computed survival with the data.

In some embodiments, the invention provides for incorporating in the treatment planning process spatial variations of cell killing within the tumor, dependence on the local energy spectrum of protons characterized by LET, and tissue specific parameters of the phenomenological model. The model uses the biological flexibility to maximize the tumor inactivation with minimal side effects. Hence, the process may include the use of two sets of tissue parameters; one for the planned treatment volume (tumor cells with α/β ratio>20), and one for the normal tissue (α/β ratio<10).

An analytic model for effective and reliable LET distribution calculation may also be used. LET models can properly account for the secondary particles due to inelastic nuclear interactions, which become increasingly important at the higher energies of interest. Identification of the most important inelastic nuclear interaction processes for the proton energy spectrum under study can be provided, along with validation of the LET computations with Monte Carlo simulations. The LET dependence on tissue parameters in the models can be mapped from the data.

To deliver a desired dose to the treatment volume, techniques from intensity modulated proton therapy (IMPT) may be used. This treatment may use a plurality of pencil proton beams (or other hadron beams) to deliver intentionally non-uniform dose distributions that superimpose to give the desired dose in the target volume. A well known 2.5D IMPT technique may be particularly useful for such a purpose.

Moreover, the intensities of the poly-energetic pencil beams used in IMPT may be individually adapted to the proximal and distal edges of the target volume to yield the desired dose based at least on the respective RBE values previously determined for these regions. The intensities of the pencil beams may serve as weights, modulated across the target volume, based in part on the variations in the RBE values. Additional weights may also be applied to the energies of the pencil beams, which increase the number of degrees of freedom and the dose shaping potential. Additionally, for the SOBP technique, the RBE values, that are different for the proximal and distal parts of the SOBP, as well as the RBE value for the declining distal edge and normal tissue (section A in FIG. 1) may be adopted into the calculation as weighting factors fixed by the bio-response model.

Thus, according to one aspect of the invention, traditional IMRT methods may be used to incorporate adequate RBE values into a treatment planning program. IMRT methods are preferred over 3-dimensional conformal radiation therapy (3DCRT) because the intensity distribution inside a single field is non-uniform, but when combined with the other beams the result is an optimal dose distribution in the patient. This feature may be most useful when taking into account the variability of RBE along the beam line.

IMRT methods for charged particles may also be preferred over traditional intensity modulated radiation therapy as applied to photons (IMXT) because the IMXT photon method is only two dimensional in nature. That is, the beam weights for a given field are, in general, modulated only in the plane perpendicular to the beam direction. This is in contrast to IMPT, for which the Bragg-peak phenomena provides three dimensional localization of the dose. This allows for modulation of a single field beam weights (intensities and energies) not only in the lateral plane, but in transverse planes as well. Hence, IMPT has extra degrees of freedom that are utilized to effectively achieve the desired dose distribution.

As an early step of developing an IMRT treatment plan based on variations in RBE throughout the proton beam path, various clinical objectives should be set, just as for any other therapy plan. This may be done either in terms of certain dose and dose-volume requirements, or biological indices such as tumor control probability (TCP) and normal tissue complication probability (NTCP). To fully optimize biological effects of the treatment, the dose and dose-volume requirements should be set in terms of biological dose ($D_{BIO}$), which may be defined as the product of respective RBE value(s) and the physical dose(s) ($D_{Physical}$). The RBE determination methods should incorporate not only RBE values for cell killing, but also, for example, the RBE values for loss of endothelial functionality and contribution of endothelial cell damage, among other biological weighting factors. An example of a method for proton IMRT treatment plan is known that is tailored to obtain a homogeneous "biological effect" expressed in terms of $S/S_0$ of linear-quadratic model discussed above (see Eq. (1)).

IMPT treatment plans may be optimized using an "inverse" treatment planning approach. If $D_{BIO}(r)$ represents the biological dose where r is the position coordinate, and a set of treatment parameters are represented by $\{w_i\}$, then formally $D_{BIO}(r)=O(r)\{w_i\}$, where O is an operator. Satisfying clinical objectives requires inversion of the treatment parameter-dose relationship; $\{w_i\}=O^{-1}(r)D_{BIO}(r)$. This is the basic idea behind the inverse planning approach used in conventional IMRT that uses the physical dose, and where $\{w_i\}$'s are lateral fluence weighting factors.

There are certain physical, practical and clinical limitations inherent to the inverse planning method that may make the dose distributions and biological indices achievable in practice different from the ones designed by the planner. Consequently, the variable treatment parameters may need to be optimized to best meet the preset clinical objectives.

To judge how well the clinical objectives are being met, an "objective function" may be used that encapsulates the requirements set forth by the planner, and describes the level of deviation from the set objectives. Naturally, the objective function will vary depending on the treatment parameters, but should have a minimum value when the treatment parameters are optimized. Thus, the optimization process becomes a mathematics problem of minimizing the objective function once this function has been constructed. Typically, during optimization a set of optimal energy fluences from each subfield are determined that yield the desired dose distribution within the SOBP region of the treatment site in the patient.

Just as the clinical objectives can be specified in terms of physical and biological parameters, the objective function (OF) as well can depend on physical and biological variables. Thus, the clinical merit of the dose distribution may be expressed by $$OF(D_{BIO}(r))=OF(\{w_i\}) \quad (3)$$

$$D_{BIO}=RBE*D_{Physical} \quad (4)$$

IMXT algorithms are usually designed to optimize the physical dose distribution, but IMPT algorithms should be designed to optimize the biological dose distribution, to take into account different RBE values present in proton therapy. The OF may still be taken in its common form as the normalized sum of squared dose deviations for all voxels of the volume under consideration. Then, for example, the well known maximum dose constraint for organs at risk (OAR) can be modified and expressed as $$OF_{MAX}^{OAR}(\{w_i\}) = \frac{1}{N^{OER}} \sum_{k=1}^{N^{OER}} [C(D_{k,BIO}^{OAR}\{w_i\} - D_{MAX}^{OAR})]^2 \quad (5)$$

Here $D_{k,BIO}^{OAR}$ is the biological dose in voxel k of OAR, $D_{MAX}^{OAR}$ is the prescribed maximum allowed dose in OAR, C is a selection operator such as C(x)=1 if x≥0, and C(x)=0 if x<0, and $N^{OAR}$ is the number of voxels in OAR. Similarly, for the target volume the familiar OF for the minimal and maximal dose limits should be modified for the RBE optimized treatment plan. OF may take the following form for the maximal and minimal dose constraints on target volume (Equations 6 and 7 respectively), $$OF_{MAX}^{Target}(\{w_i\}) = \frac{1}{N^{Target}} \sum_{k=1}^{N^{Target}} [C(D_{k,BIO}^{Target}\{w_i\} - D_{MAX}^{Target})]^2 \quad (6)$$

$$OF_{MIN}^{Target}(\{w_i\}) = \frac{1}{N^{Target}} \sum_{k=1}^{N^{Target}} [C(D_{MIN}^{Target}\{w_i\} - D_{k,BIO}^{Target})]^2 \quad (7)$$

Here $D_{k,BIO}^{Target}$ is the biological dose in voxel k of the target volume, $D_{MAX}^{Target}$ and $D_{MIN}^{Target}$ are the prescribed maximum and minimum allowed doses in the target volume. Thus, the physician may still give the treatment prescription in terms of photon dose (say in cobalt-gray equivalents) coming from vast experience with treating with photons, the method of treatment should optimize the treatment plan to achieve the clinical objectives through true biological dose and effect by employing RBE values determined by a combination of methods described earlier. The methods for treatment optimization described herein are flexible and may be adapted accordingly to changes in clinical objective specification.

Inverse planning tools used in IMXT and IMPT in most cases are the same, or at least similar. The skilled artisan will therefore recognize that when developing IMPT algorithms, one can use IMXT programs and/or the existing IMXT codes as a starting point.

Figure 2:
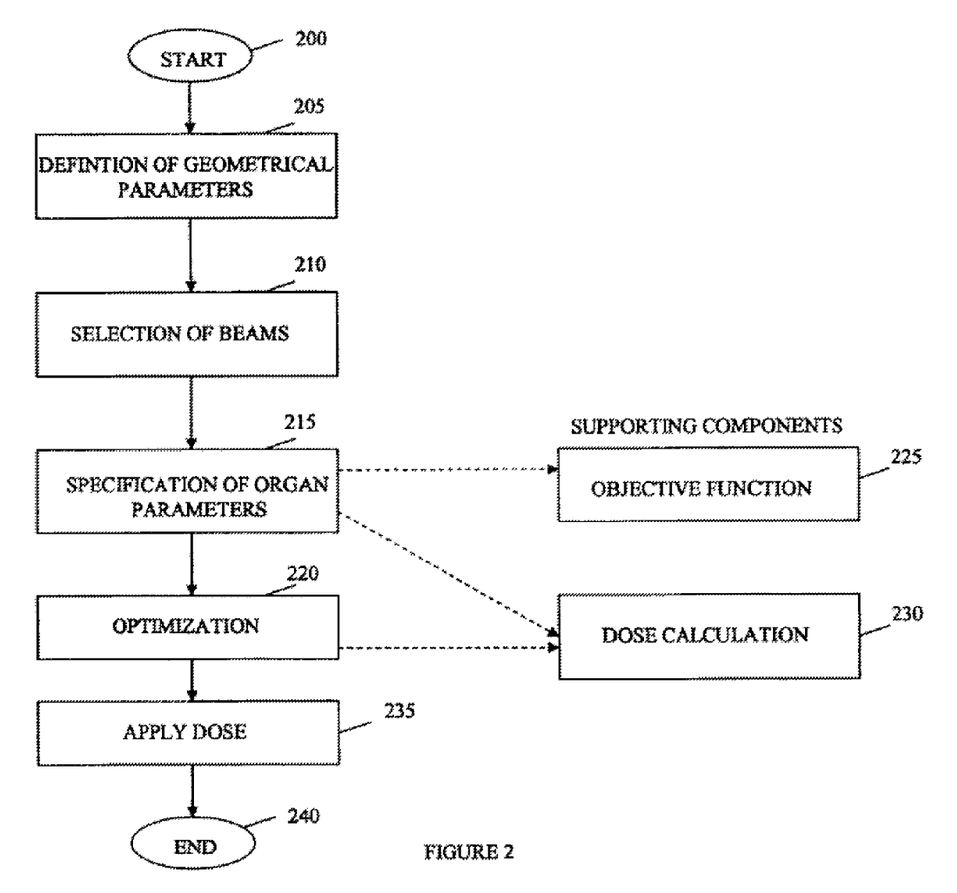
FIG. 2 is a flow diagram showing steps of treatment planning, according to principles of the invention.

The conventional IMRT treatment planning process may be subdivided into steps shown in FIG. 2, starting at step 200. FIG. 2 also shows several exemplary components, objective function 225 that encapsulates the requirements set forth by the planner and describes or calculates the level of deviation from the set objectives, and dose calculation 230 of the treatment algorithm modules provides the necessary calculations to determine an effective dose based in part on biological factors.

Continuing with step 205, geometrical parameters related to the treatment site are defined, such as dimensions of the elemental fluence amplitudes projected on the isocenter plane. At step 210, selection of the appropriate beam configuration is made, defining such parameters as the number of treatment beam ports and their respective beam angles, for example. At step 215, organ parameters, such as dose-volume constraints, and/or tissue parameters are specified. Optimization at step 220 represents an iterative process of finding a set of treatment parameters that minimizes the objective function 225, which may be defined, for example, as in equations 3 through 7. For a set of treatment parameters at each step of iteration dose calculation component 230 may supply for each voxel of the volume being irradiated and for each irradiation subfield the biological dose ($D_{BIO}$ as defined earlier in Equation 4) as input for objective function 225. Dose calculation component 230 may use as input the tissue parameters specified in step 215. When the optimization loop yields a set of parameters that minimizes the objective function 225, the corresponding output of the dose calculation component 220 may be presented to the user in the form of biological dose volume histograms for evaluation of the treatment plan. Continuing with step 235, the calculated dose may be applied per the treatment plan. At step 240, the process ends.

Figure 3:
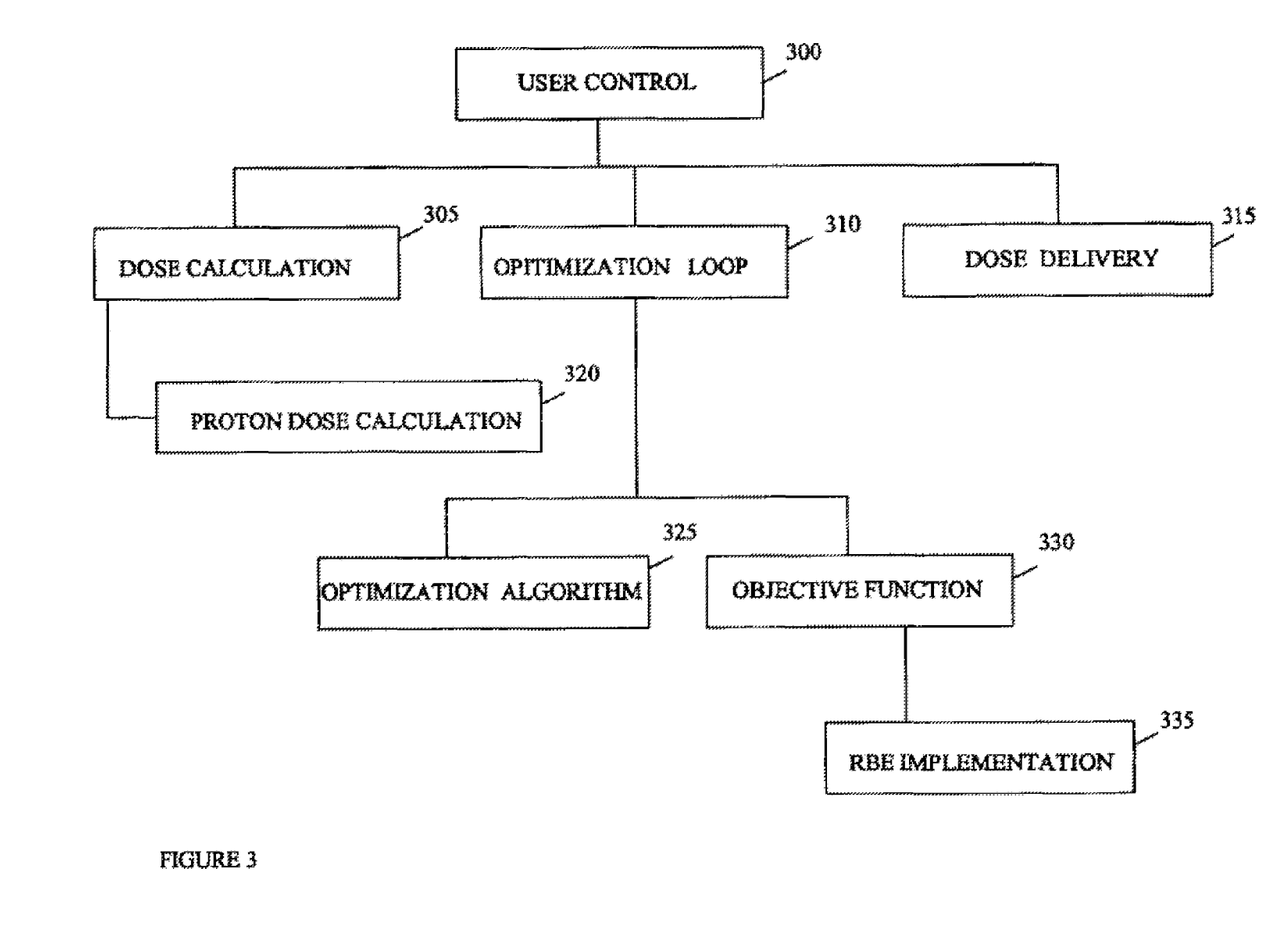
FIG. 3 is a relational block diagram showing various exemplary components of an embodiment of the invention.

FIG. 3 is a relational block diagram showing the separation of the treatment planning algorithm into semi-independent modules or components, according to principles of the invention. These modules may be implemented on any suitable computer readable medium for execution. The modules include a user control module 300 for interacting with a user who may be constructing a treatment plan. A dose calculation module 305 provides the necessary calculations to determine an effective dose based in part on biological factors, as appropriate, and calls upon a proton dose calculation module 320 for treatments using proton beams (likewise other modules for other hadron beams may be called upon).

The optimization loop module 310 calls upon an optimization algorithm 325 and an objective function module 330, which in turn may call upon a RBE implementation module 335 for calculating the various RBE values, as discussed previously. The objective function component 330 takes into account the biological dose like in the examples presented by Equations 3 through 7. The proton dose calculation component 320 should incorporate the LET and RBE determination models. This proton dose calculation component 320 (or equivalent hadron dose module) may have in its output, as one example, a matrix $D_{i,j}^{BIO}$ of normalized biological dose values in voxel i from beam spot j, as opposed to physical dose matrix $D_{i,j}^{Photon}$ of conventional treatment plans.

Figure 4:
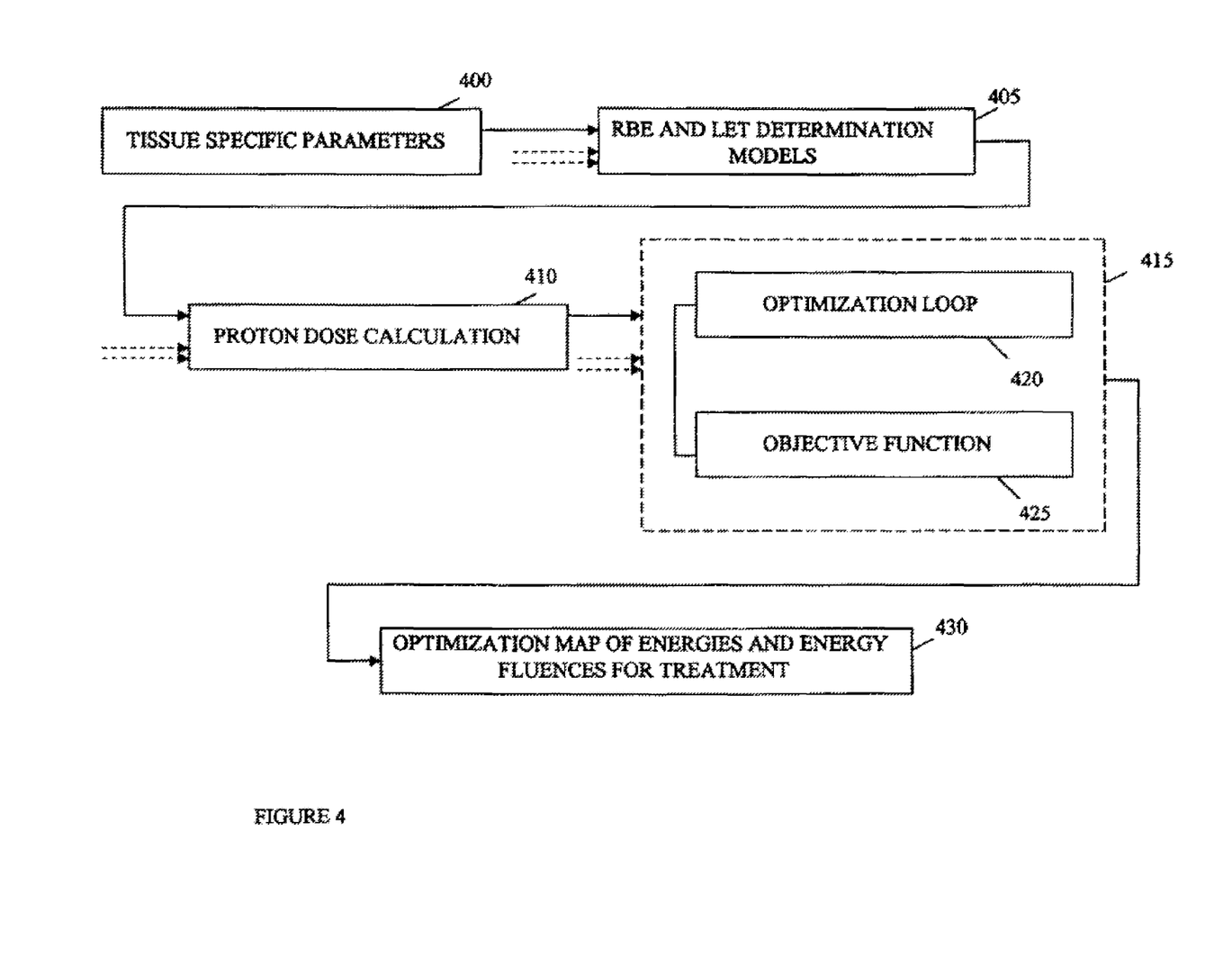
FIG. 4 is a combined relational block diagram and flow diagram of an embodiment of the invention, showing exemplary components and exemplary sequencing of processing.

FIG. 4 shows exemplary components employed in the general flow of the treatment planning process of the invention, which may be implemented on a suitable computing platform having memories, storage, processors and input/output interfaces as is commonly known in the art. Tissue specific parameters 400 that describe the site under treatment (such as an organ, for example) may be feed into an RBE and LET determination model(s) 405, which may also determine the variability of RBE. A proton dose calculation module 410 calculates a proton biological dose based on the RBE and LET determination. An optimization process 415 employs an optimization loop 420 and an objective function 425 to provide an optimized map of energies and energy fluences for treatment 430 including adjusting an intensity and energy of each of the beams at each of the plurality of SOBP sections.

Figure 5:
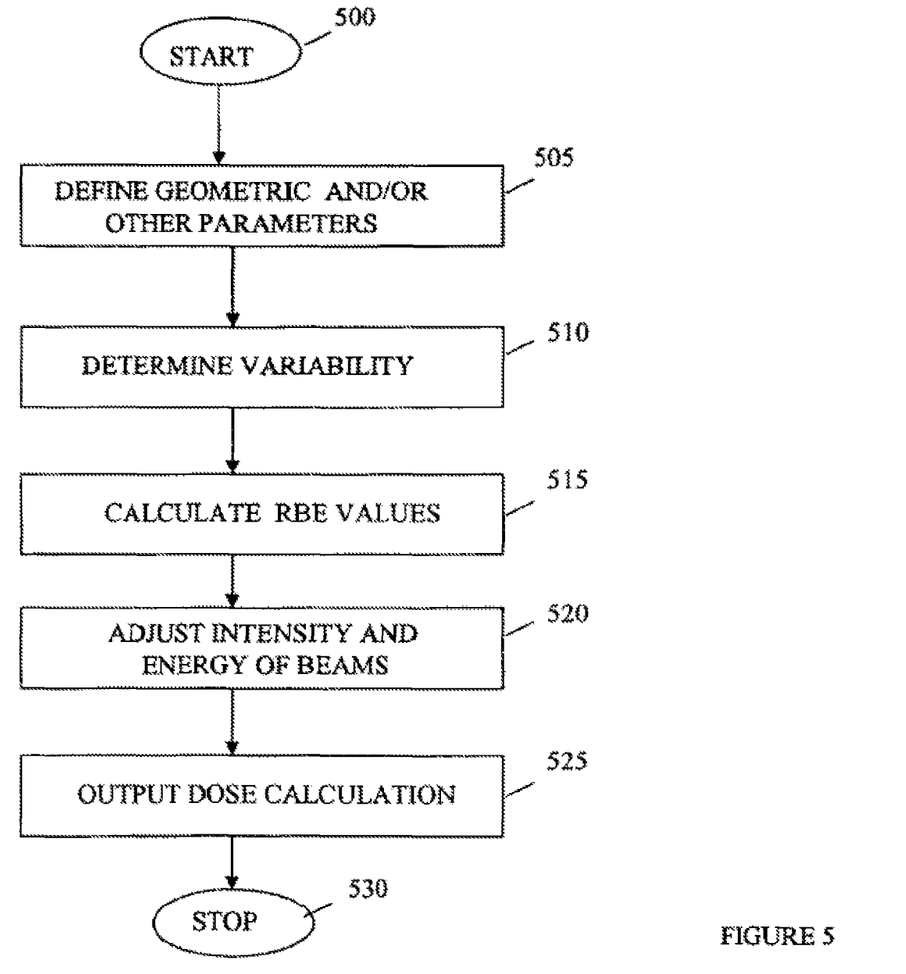
FIG. 5 is a flow diagram showing steps of an embodiment of using the invention.

FIG. 5 is a flow diagram showing steps of an embodiment of using the invention, starting at step 500. At step 505, the geometric parameter of the treatment site may be defined. For example, these parameters may include dimensions of the elemental fluence amplitudes projected on the isocenter plane. Other parameters such as tissue parameters may also be defined. At step 510, the variability of relative biological effectiveness (RBE) along a line of each of the plurality of beams (hadron, carbon ion, or proton beams) may be determined. At step 515, RBE values may be calculated that takes into account the determined variability for each of the plurality of SOBP sections. The SOBP sections may include the declining distal edge and at least one other section of the SOBP. At step 520, the intensity and energy of the plurality of beams may be adjusted based on the calculated RBE values. At step 525, the biological dose calculations may be output for use in treating a patient by irradiation. The output may be in the form of a histogram, for example. At step 530, the process ends.

The innovations provided by the invention typically require accurate proton dose (or other hadron dose) measurements. A reliable beam calibration, of course, is also necessary. The desired accuracy of the proton dose measurements in radiotherapy applications is ±3%. The measurements are also typically required to be reproducible within ±2%.

The International Commission on Radiation Units and Measurements (ICRU) has published a proton dosimetry protocol. A proton dosimetry intercomparison based on the ICRU report 59 protocol was done at Luma Linda University Medical Center. Eleven institutions participated in the intercomparison. It was shown that use of the ICRU report 59 protocol would result in absorbed doses being delivered to patients at their institutions to within ±0.9% (one standard deviation). The maximum difference between determined doses was less than 3%. These results were obtained with the use of thimble ionization chambers with $^{60}$Co calibration factors traceable to standard laboratories. The ICRU report 59 protocol has been adopted by most proton therapy centers. A thimble ionization chamber may be a practical instrument for determining the reference absorbed dose.

Various modifications and variations of the described methods and systems of the invention will be apparent to those skilled in the art without departing from the scope and spirit of the invention. Any document or patent referred to herein is incorporated by reference. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. An apparatus for treatment planning for delivering a biological dose at a treatment site of a patient, the apparatus comprising:
   a first component to determine a variability of relative biological effectiveness (RBE) along a line of a plurality of hadron beams, wherein RBE is a ratio of a dose of reference radiation to a hadron dose required to achieve an equivalent biological effect;
   a second component to calculate RBE values at a plurality of sections of a spread-out Bragg peak (SOBP) associated with the treatment site, taking into account the determined variability from the first component; and
   wherein the plurality of sections include: a declining distal edge area of the SOBP and at least one of: a proximal area of the SOBP, a distal area of the SOBP, a pre-plateau area of the SOBP, and wherein the calculated biological dose distributions superimpose for providing a desired biological dose at the treatment site.

2. The apparatus of claim 1, further comprising a third component to adjust an intensity and energy of at least one of the plurality of hadron beams at each of the plurality of sections of the associated spread-out Bragg peak (SOBP) based on respective calculated RBE values for each of the plurality of sections to provide a calculated biological dose distribution for each of the plurality of sections.

3. The apparatus of claim 2, wherein the third component calculates a biological dose in voxels of each of the plurality of sections associated with the treatment site.

4. The apparatus of claim 2, wherein the plurality of hadron beams comprise a plurality of proton beams.

5. The apparatus of claim 2, wherein the plurality of hadron beams comprise a plurality of carbon ion beams.

6. The apparatus of claim 2, further comprising a fourth component to manage tissue specific parameters and to provide the tissue specific parameters to the first component to be used in determining the variability of (RBE) and to provide the tissue specific parameters to the second component to calculate RBE values.

7. The apparatus of claim 6, wherein the tissue specific parameters includes parameters for at least one of: human fibroblasts and tumor cells.

8. The apparatus of claim 2, wherein the plurality of hadron beams include a pencil beam.

9. The apparatus of claim 8, wherein the pencil beam comprises a poly-energetic pencil beam.

10. The apparatus of claim 1, wherein the biological effect includes at least any one of: cell killing, cell repair capacity, endothelial functionality, and specific constraints from organs at risk.

* * * * *